(12) United States Patent
Ogura

(10) Patent No.: US 7,022,084 B2
(45) Date of Patent: Apr. 4, 2006

(54) HEART-SOUND DETECTING APPARATUS AND HEART-SOUND DETECTING METHOD

(75) Inventor: Toshihiko Ogura, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 0 days.

(21) Appl. No.: 11/027,994

(22) Filed: Jan. 4, 2005

(65) Prior Publication Data
US 2005/0124905 A1 Jun. 9, 2005

Related U.S. Application Data

(60) Division of application No. 10/639,463, filed on Aug. 13, 2003, now abandoned, which is a continuation-in-part of application No. 09/942,865, filed on Aug. 31, 2001, now abandoned.

(30) Foreign Application Priority Data
Feb. 7, 2001 (JP) ............................. 2001-030879

(51) Int. Cl.
*A61B 5/02* (2006.01)

(52) U.S. Cl. .................. 600/528; 600/485; 600/500

(58) Field of Classification Search .................. 600/528
See application file for complete search history.

(56) References Cited

U.S. PATENT DOCUMENTS

| | | | |
|---|---|---|---|
| 3,978,848 A | 9/1976 | Yen et al. | |
| 4,105,020 A | 8/1978 | Matsuoka et al. | |
| 4,248,241 A | 2/1981 | Tacchi | |
| 4,290,434 A | 9/1981 | Jewett | |
| 4,331,156 A | 5/1982 | Apple et al. | |
| 4,938,227 A | 7/1990 | Niwa et al. | |
| 5,031,630 A | 7/1991 | Hirano et al. | |
| 5,243,992 A * | 9/1993 | Eckerle et al. | 600/503 |
| 5,293,874 A * | 3/1994 | Takahashi et al. | 600/500 |
| 5,365,937 A | 11/1994 | Reeves et al. | |
| 5,406,953 A | 4/1995 | Bui | |
| 5,551,438 A | 9/1996 | Moses | |
| 5,687,738 A | 11/1997 | Shapiro et al. | |
| 5,743,857 A | 4/1998 | Shinoda et al. | |
| 5,807,267 A | 9/1998 | Bryars et al. | |
| 5,868,679 A | 2/1999 | Miyazaki | |

(Continued)

FOREIGN PATENT DOCUMENTS

FR 2 535 964 A1 5/1984

(Continued)

OTHER PUBLICATIONS

U.S. Appl. No. 09/942,864, filed Aug. 2001, Narimatsu et al.

(Continued)

*Primary Examiner*—Max F. Hindenburg
*Assistant Examiner*—Patricia Mallari
(74) *Attorney, Agent, or Firm*—Oliff & Berridge, PLC

(57) ABSTRACT

An apparatus for detecting a heart sound of a living subject, including a pressure-pulse-wave sensor which is adapted to be worn on a body portion of the subject that is distant from a chest of the subject, detects a pressure pulse wave produced by an artery of the body portion, and generates a pressure-pulse-wave signal representing the detected pressure pulse wave; and a heart-sound extracting device for extracting, from the pressure-pulse-wave signal generated by the pressure-pulse-wave sensor, a heart-sound component representing the heart sound of the subject.

2 Claims, 8 Drawing Sheets

U.S. PATENT DOCUMENTS

| | | |
|---|---|---|
| 5,957,866 A | 9/1999 | Shapiro et al. |
| 6,021,351 A | 2/2000 | Kadhiresan et al. |

FOREIGN PATENT DOCUMENTS

| | | |
|---|---|---|
| JP | A-52-108684 | 9/1977 |
| JP | A-52-146987 | 12/1977 |
| JP | U-60-106607 | 7/1985 |
| JP | A-62-27922 | 2/1987 |
| JP | 63-293424 | 11/1988 |
| JP | A-1-502001 | 7/1989 |
| JP | A-2-203869 | 8/1990 |
| JP | U-8-675 | 4/1996 |
| JP | A-10-295657 | 11/1998 |
| JP | B2-2877950 | 1/1999 |
| WO | WO 88/05283 | 7/1988 |

OTHER PUBLICATIONS

Circulatory-Organ Function Test (Chapter 18); Froelicher et al.; Cardiac Disease; Year Book Med. Publ., Inc.; 1986; pp. 1508-1511.

* cited by examiner

HEART-SOUND DETECTING APPARATUS AND HEART-SOUND DETECTING METHOD

This a Division of application Ser. No. 10/639,463 filed Aug. 13, 2003, abandoned which in turn is a Continuation-In-Part of application Ser. No. 09/942,865 filed Aug. 31, 2001 abandonded. The entire disclosure of the prior applications is hereby incorporated by reference herein in its entirety.

BACKGROUND OF THE INVENTION

1. Field of the Invention

The present invention relates to an apparatus and a method for detecting a heart sound of a living subject, at a position distant from a chest of the subject.

2. Related Art Statement

Heart sounds are used to make a diagnosis of heart-valve disease or congenital heart disease. In addition, heart sounds may be used to obtain pulse-wave-propagation-velocity-relating information such as a pulse-wave propagation needed for a pulse wave to propagate through an artery between two body portions of a living subject, or a pulse-wave propagation velocity at which a pulse wave propagates through an artery.

It has been a conventional manner to detect heart sounds using a microphone. Since heart sounds are vibrations, blood-flow sounds, etc. produced when the valves of the heart open and close, the heart-sound microphone is usually put on the skin of the chest (in particular, the skin right above the heart).

Therefore, when the heart-sound microphone is put on, it is needed to take off cloths to expose the chest. Thus, putting on the heart-sound microphone is more cumbersome than putting on a sensor on an arm or a neck.

Meanwhile, obtaining pulse-wave-propagation-velocity-relating information needs detecting respective heartbeat-synchronous signals at two body portions of a living subject. Therefore, in the case where the heart sound detected by the microphone put on the chest is used as one of the two heartbeat-synchronous signals needed to obtain the pulse-wave-propagation-velocity-relating information, it is disadvantageously needed to put on another sensor on the subject so as to detect the other heartbeat-synchronous signal.

SUMMARY OF THE INVENTION

It is therefore an object of the present invention to provide a heart-sound detecting apparatus for detecting a heart sound at a position distant from a chest of a living subject; a heart-sound detecting method of detecting a heart sound at a position distant from a chest of a living subject; a pulse-wave-propagation-velocity-relating-information obtaining apparatus including the heart-sound detecting apparatus which allows a sensor thereof to be easily worn; and a blood-pressure measuring apparatus capable of detecting a heart sound.

The above object has been achieved by the present invention. According to a first feature of the present invention, there is provided an apparatus for an apparatus for detecting a heart sound of a living subject, comprising a pressure-pulse-wave sensor which is adapted to be worn on a body portion of the subject that is distant from a chest of the subject, detects a pressure pulse wave produced by an artery of the body portion, and generates a pressure-pulse-wave signal representing the detected pressure pulse wave; and a heart-sound extracting means for extracting, from the pressure-pulse-wave signal generated by the pressure-pulse-wave sensor, a heart-sound component representing the heart sound of the subject.

According to this feature, the heart-sound extracting means extracts, from the pressure-pulse-wave signal generated by the pressure-pulse-wave sensor worn on the body portion distant from the chest, the heart-sound component representing the heart sound. Thus, the present apparatus can detect a heart sound at a position distant from a chest of a living subject.

According to a second feature of the present invention, there is provided an apparatus for detecting a heart sound of a living subject, comprising a pressure-pulse-wave sensor which is adapted to be worn on a body portion of the subject that is distant from a chest of the subject, and includes a plurality of pressure sensing elements arranged in a widthwise direction of an artery of the body portion, each of the pressure sensing elements detecting a pressure pulse wave produced by the artery of the body portion, and generating a pressure-pulse-wave signal representing the detected pressure pulse wave; an optimum-element selecting means for selecting one of the pressure sensing elements, as an optimum pressure sensing element, based on respective magnitudes of the respective pressure-pulse-wave signals generated by the pressure sensing elements; and a heart-sound extracting means for extracting, from the pressure-pulse-wave signal generated by the optimum pressure sensing element, a heart-sound component representing the heart sound of the subject.

According to this feature, the optimum-element selecting means selects, from the pressure sensing elements, the optimum pressure sensing element that can detect, with high sensitivity, the pressure pulse wave, and the heart-sound extracting means extracts, from the pressure-pulse-wave signal generated by the optimum pressure sensing element, the heart-sound component representing the heart sound of the subject. Thus, the present apparatus can detect a heart sound having a clear waveform. In order to detect a heart sound having a clear waveform, it is needed to position a pressing sensing element right above a target artery. However, since the artery is present under the skin and accordingly is not visible, and additionally, since the artery may move because of the pressing of the pressure-pulse-wave sensor and/or the motion of the body, it is difficult to accurately position a single pressure sensing element right above, or in the vicinity of, a target artery. If the pressure sensing element is not positioned right above, or in the vicinity of, the target artery, the heart sound extracted from the pressure-pulse-wave signal supplied from the pressure sensing element may not have a clear waveform.

According to a third feature of the present invention, there is provided an apparatus for obtaining information relating to a velocity at which a pulse wave propagates through an artery of a living subject, the apparatus comprising a heart-sound detecting apparatus according to the first or second feature; and an information obtaining means for obtaining the information based on a first timing at which the pressure-pulse-wave sensor of the heart-sound detecting apparatus detects a prescribed periodic portion of the heart sound, and a second timing at which the pressure-pulse-wave sensor detects a prescribed periodic portion of the pressure pulse wave.

According to this feature, the pressure-pulse-wave sensor of the heart-sound detecting apparatus detects two heartbeat-synchronous signals, i.e., the heart sound and the pressure pulse wave, and the information obtaining means obtains the information based on the heart sound and the pressure pulse wave. Thus, the single pressure-pulse-wave sensor suffices for obtaining the pulse-wave-propagation-velocity-relating information. The single sensor is easily worn on the subject.

According to a fourth feature of the present invention, there is provided an apparatus for measuring a blood pressure of a living subject, comprising an inflatable cuff which is adapted to be wound around an upper arm of the subject; a blood-pressure determining means for determining the blood pressure of the subject based on a signal which is produced in the cuff while a pressing pressure of the cuff is gradually changed; a pressure-pulse-wave sensor which is provided in an inner surface of the cuff, detects a pressure pulse wave produced by an artery of the upper arm, and generates a pressure-pulse-wave signal representing the detected pressure pulse wave; and a heart-sound extracting means for extracting, from the pressure-pulse-wave signal generated by the pressure-pulse-wave sensor, a heart-sound component representing the heart sound of the subject.

According to this feature, when the cuff is wound around the upper arm to measure a blood pressure of the subject, the pressure-pulse-wave sensor to detect the heart sound is naturally worn on the subject. In addition, since the cuff is wound around the upper arm such that the cuff closely contacts the arm, that the cuff is wound around the upper arm means that the pressure-pulse-wave sensor is appropriately worn on the arm.

According to a fifth feature of the present invention, there is provided a method of detecting a heart sound of a living subject, comprising the steps of wearing the pressure-pulse-wave sensor of the heart-sound detecting apparatus according to the first or second feature, on a body portion of the subject that is distant from a chest of the subject, so that the pressure-pulse-wave sensor detects a pressure pulse wave produced by an artery of the body portion, and generates a pressure-pulse-wave signal representing the detected pressure pulse wave, and extracting, from the pressure-pulse-wave signal generated by the pressure-pulse-wave sensor, a heart-sound component representing the heart sound of the subject.

According to this feature, the heart-sound component representing the heart sound is extracted from the pressure-pulse-wave signal generated by the pressure-pulse-wave sensor worn on the body portion distant from the chest. Therefore, the heart sound can be detected at a position distant from the chest.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
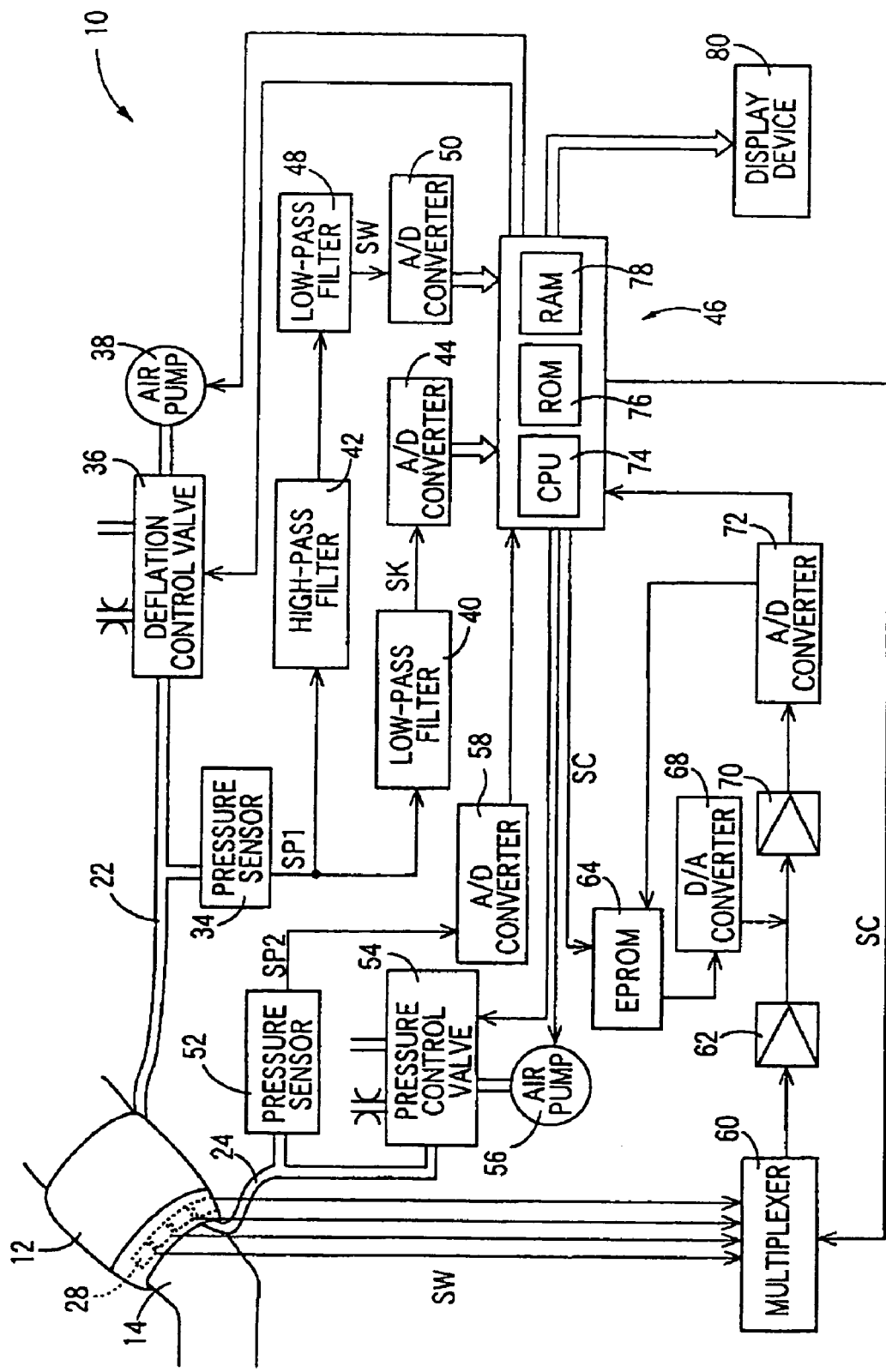
FIG. 1 is a diagrammatic view for explaining a construction of a physical-information obtaining apparatus functioning as a heart-sound detecting apparatus, a blood-pressure measuring apparatus, and a pulse-wave-propagation-velocity-relating-information obtaining apparatus, to which the present invention is applied.

Hereinafter, there will be described a preferred embodiment of the present invention in detail by reference to the accompanying drawings. FIG. 1 shows a diagrammatic view for explaining a construction of a physical-information obtaining apparatus 10 functioning as a heart-sound detecting apparatus, a blood-pressure measuring apparatus, and a pulse-wave-propagation-velocity-relating-information obtaining apparatus, to which the present invention is applied.

Figure 2:
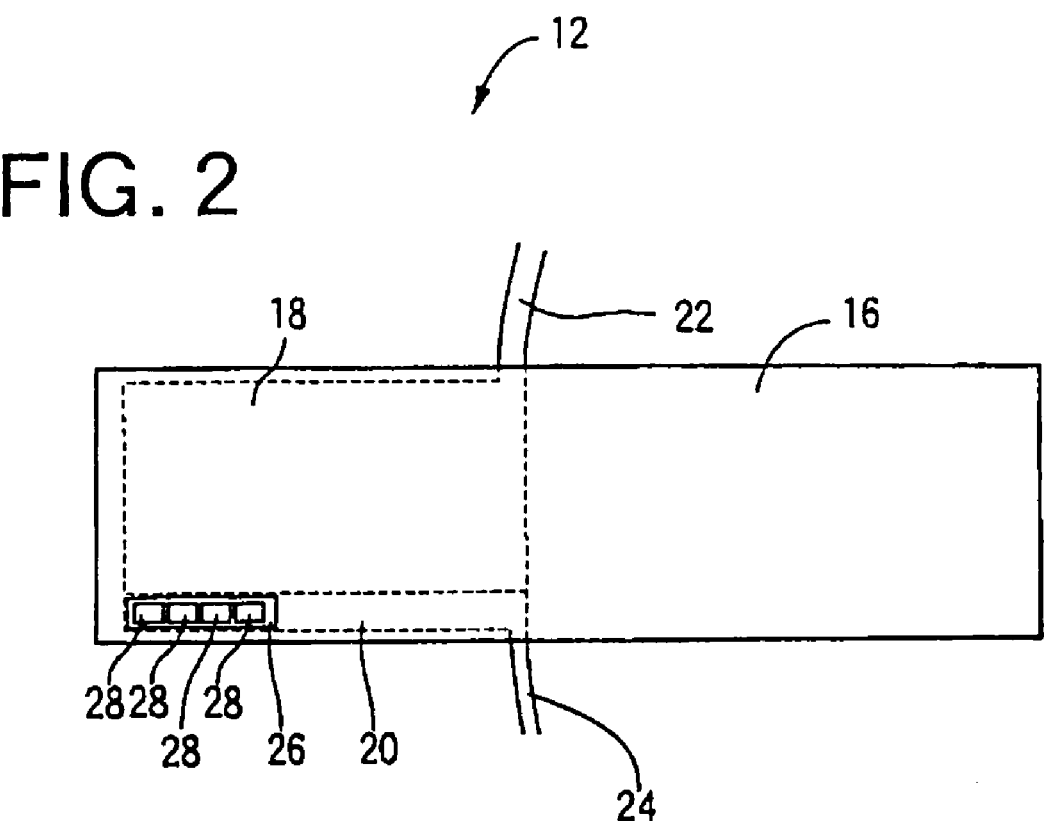
FIG. 2 is a development view of an inflatable cuff of the apparatus of FIG. 1.

In FIG. 1, reference numeral 12 designates an inflatable cuff which is adapted to be wound around a right upper arm 14 of a patient. FIG. 2 is a development view of the cuff 12. As shown in FIG. 2, the cuff 12 includes a belt-like cover bag 16 which is formed of a non-stretchable and considerably rigid cloth and has substantially the same length as that of a common inflatable cuff which is used to measure a blood pressure of an upper arm of a patient. However, a width of the cuff 12 is longer than that of the common cuff by a length corresponding to a width of a small cuff 20, described below.

In the cover bag 16, there are provided a large cuff 18 and the small cuff 20 each of which has substantially the same length (e.g., 24 cm) as that of a circumferential length of the upper arm 14 and is formed of rubber. The large cuff 18 has substantially the same width as that of a rubber bag employed in the common cuff. The width of the small cuff 20 is smaller than that of the large cuff 18 and is, for example, 2 cm. The large cuff 18 and the small cuff 20 are provided such that respective one long sides thereof are adjacent to each other. In a state in which the cuff 12 is wound around the upper arm 14, the small cuff 20 is positioned at a distal-side end of the cuff 12. The large cuff 18 and the small cuff 20 are connected to respective pipings 22, 24 for supplying pressurized air thereto.

A flexible support plate 26 which has substantially the same width as that of the small cuff 20 is fixed to an inner surface of the cuff 12 that contacts the upper arm 14 when the cuff 12 is wound around the same 14. More specifically described, the support plate 26 is fixed to a portion of the inner surface of the cuff 12 that corresponds to the small cuff 20, so that when the cuff 12 is wound around the upper arm 14, the support plate 26 is pressed by the small cuff 20. The support plate 26 supports four pressure-pulse-wave sensors 28 such that the four sensors 28 are arranged along a straight line in a lengthwise direction of the plate 26. Between each pair of adjacent sensors 28, there is provided a considerably small space of 0.9 mm length.

Figure 3:
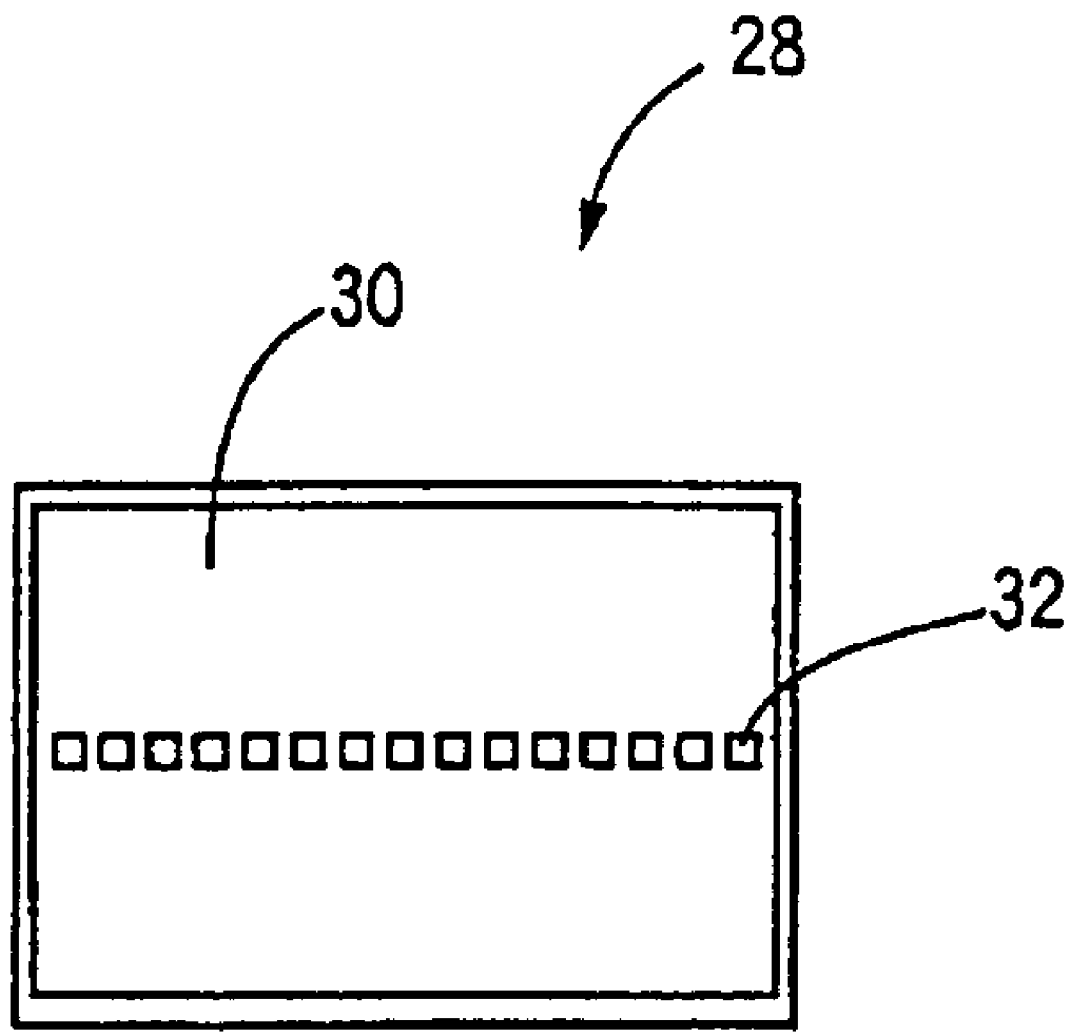
FIG. 3 is a plan view of a pressure-pulse-wave sensor of the apparatus of FIG. 1.

FIG. 3 is a plan view of one of the four pressure-pulse-wave sensors 28. The sensor 28 has a press surface 30 which is defined by a semiconductor chip such as monocrystalline silicon and has a length of about 13 mm in a lengthwise direction of the cuff 12 (i.e., in a left-right direction in FIG. 3). In the press surface 30, there are provided a number of semiconductor-based pressure sensing elements (or pressure detecting elements) 32 at a regular interval of distance along a straight line in the lengthwise direction of the cuff 12. In the present embodiment, each pressure-pulse-wave sensor 28 has fifteen pressure sensing elements 32 which are arranged at a regular spacing interval of 0.2 mm.

Back to FIG. 1, the large cuff 18 is connected to a pressure sensor 34, a deflation control valve 36, and an air pump 38 via the piping 22. The deflation control valve 36 is selectively placed in a pressure-supply position in which the control valve 36 permits a pressurized air to be supplied from the air pump 38 to the large cuff 18, a slow-deflation position in which the control valve 18 permits the pressurized air to be slowly discharged from the large cuff 18, and a quick-deflation position in which the control valve 36 permits the pressurized air to be quickly discharged from the large cuff 18.

The pressure sensor 34 detects an air pressure $P_{K1}$ in the large cuff 18, and supplies a first pressure signal $SP_1$ representing the detected pressure $P_{K1}$, to each of a low-pass filter 40 and a high-pass filter 42 via an amplifier, not shown. The low-pass filter 40 extracts, from the pressure signal $SP_1$, a static-pressure component contained in the signal $SP_1$, i.e., a cuff-pressure signal SK representing the pressing pressure of the large cuff 18. The cuff-pressure signal SK is supplied to a control device 46 via an A/D (analog-to-digital) converter 44. The high-pass filter 42 extracts, from the pressure signal $SP_1$, an alternating component having frequencies not lower than 0.8 Hz, and supplies the thus extracted alternating-component signal to a low-pass filter 48 via an amplifier, not shown. The low-pass filter 48 extracts, from the alternating-component signal supplied from the high-pass filter 42, an alternating component having frequencies not higher than 10.8 Hz. This alternating-component signal provides a cuff-pulse-wave signal SW representing the alternating component of the pressure signal $SP_1$. The cuff-pulse-wave signal SW is supplied to the control device 46 via an A/D converter 50.

The small cuff 20 is connected to a pressure sensor 52, a pressure control valve 54, and an air pump 56 via the piping 24. The pressure sensor 52 detects an air pressure $P_{K2}$ in the small cuff 20, and supplies a second pressure signal $SP_2$ representing the detected pressure $P_{K2}$, to the control device 46 via an A/D converter 50. The pressure control valve 54 changes the pressure of the pressurized air supplied from the air pump 56, and supplies the pressurized air having the thus changed pressure to the small cuff 20.

A multiplexer 60 sequentially supplies, according to a switch signal SC supplied from the control device 46, the respective pressure-pulse-wave signals SM supplied from the sixty pressure sensing elements 32 of the four pressure-pulse-wave sensors 28, each signal SM for a prescribed time duration, to an amplifier 62. An EPROM (erasable programmable ROM) 64 stores, for the sixty pressure sensing elements 32, respective correction signals for eliminating respective individual sensitivity differences among the pressure sensing elements 32, and sequentially supplies, according to the switch signal SC supplied from the control device 46, i.e., in synchronism with the respective switching operations of the multiplexer 60, the respective correction signals, to a D/A (digital-to-analog) converter 68, in such a manner that the respective correction signals sequentially correspond to the respective pressure sensing elements 32 supplying the respective pressure-pulse-wave signals SM being currently dealt with by the multiplexer 60.

Each of the sixty pressure-pulse-wave signals SM that have been amplified by the amplifier 62, and a corresponding one of the sixty correction signals that have been converted to respective analog signals by the D/A converter 68 are supplied to an amplifier 70. Thus, the sixty corrected pressure-pulse-wave signals SM supplied to the amplifier 70 have a uniform sensitivity. Each of the sixty corrected pressure-pulse-wave signals SM is supplied to an I/O (input-and-output) port of the control device 46 via an A/D converter 72.

The control device 46 is provided by a so-called microcomputer including a CPU (central processing unit) 74, a ROM (read only memory) 76, and a RAM (random access memory) 78. The CPU 29 processes signals according to the control programs pre-stored in the ROM 76 by utilizing the temporary-storage function of the RAM 78, and controls the deflation control valve 36 and the air pump 38 to carry out a blood-measure measurement, controls the pressure control valve 54 and the air pump 56 to carry out a heart-sound detection, determines a blood-pressure value BP, extracts a heart sound, determines a pulse-wave-propagation velocity PWV, and controls a display device 80 to display the thus determined blood-pressure value BP and pulse-wave-propagation velocity PWV.

Figure 4:
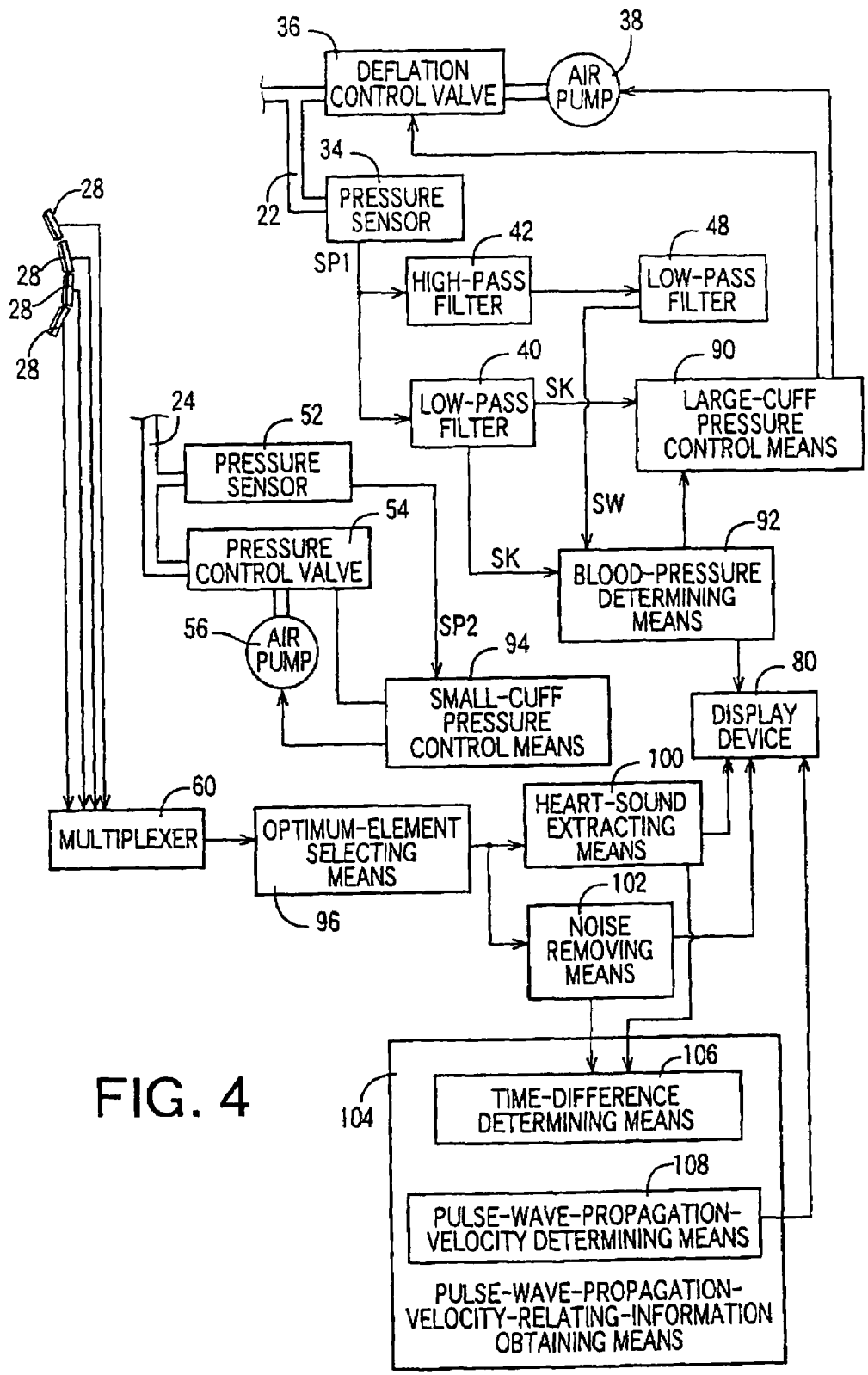
FIG. 4 is a block diagram for explaining essential functions of a control device of the apparatus of FIG. 1.

FIG. 4 is a block diagram for explaining essential functions of the control device 46. In the figure, a large-cuff-pressure control means 90 controls the deflation control valve 36 and the air pump 38 to quickly increase the pressing pressure of the large cuff 18 up to a prescribed target pressure $PM_1$, e.g., 180 mmHg and then slowly decrease the pressing pressure at a rate of from 2 to 3 mmHg/sec. After a blood-pressure determining means 92 determines a blood pressure BP of the patient, the large-cuff-pressure control means 90 releases the pressing pressure into the atmosphere, i.e., decreases the pressing pressure down to the atmospheric pressure.

The blood-pressure determining means 92 determines, based on the change of the cuff-pulse-wave signal SW obtained during the slow deflation of the pressing pressure of the large cuff 18 by the large-cuff-pressure control means 90, a systolic blood pressure BP(SYS), a mean blood pressure BP(MEAN), and a diastolic blood pressure BP(DIS) of the patient, according to well-known oscillometric method, and controls the display device 80 to display the thus determined blood pressure values.

A small-cuff-pressure control means 94 controls, based on the second pressure signal $SP_2$ supplied from the pressure sensor 52, the pressure control valve 54 and the air pump 56 to increase the air pressure $PK_2$ in the small cuff 20 up to a prescribed target pressure $PM_2$ and then keep the pressure $PK_2$ at the target pressure $PM_2$. The target pressure $PM_2$ is prescribed at such a value which assures that the press surface 30 which is provided on the inner surface of the cuff 12 and to which the pressure-pulse-wave sensors 28 are fixed, is pressed against the upper arm 14, but does not occlude the flow of blood through a brachial artery 98 of the upper arm 14.

Figure 5:
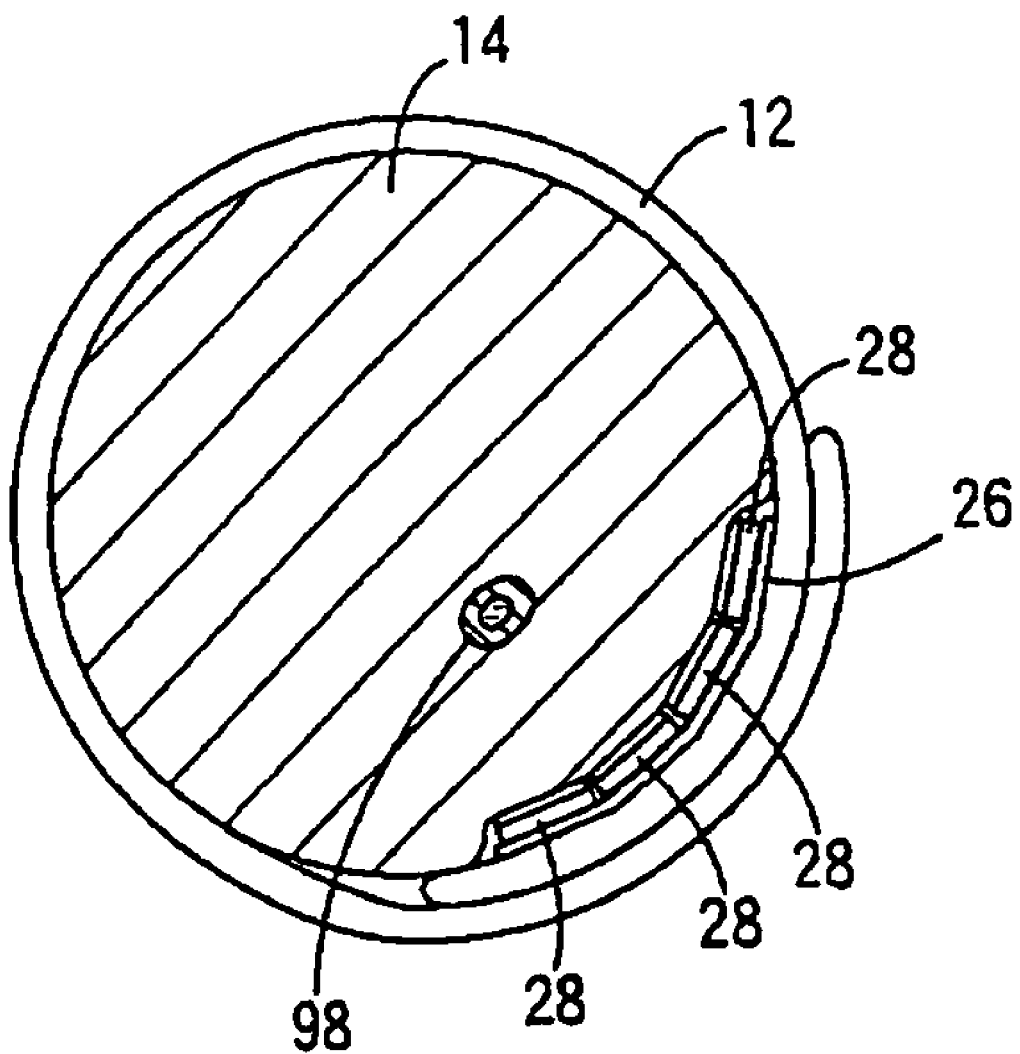
FIG. 5 is a cross-section view for explaining a state in which the cuff is wound around an upper arm of a living subject.
Figure 6:
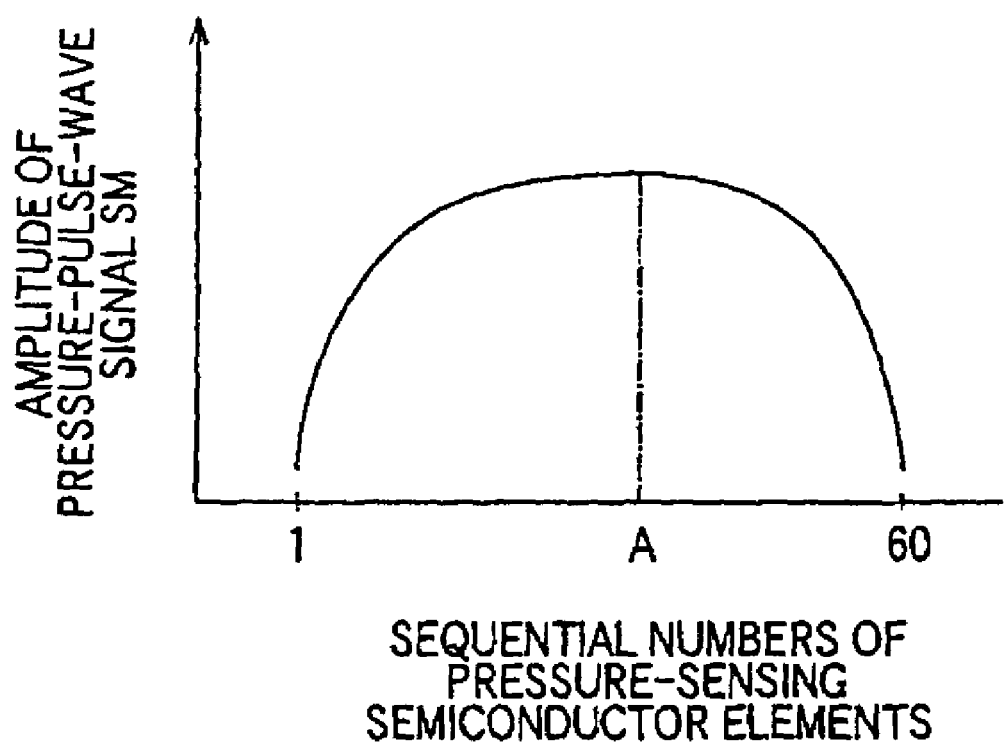
FIG. 6 is a graph showing a relationship between individual pressure-sensing semiconductor elements and respective amplitudes of respective pressure-pulse-wave signals SM generated by the individual pressure-sensing elements.

An optimum-element selecting means 96 selects, from the sixty pressure-sensing semiconductor elements 32 of the four pressure-pulse-wave sensors 28, an optimum pressure-sensing element 32 that is the most appropriate to detect heart sounds (hereinafter, referred to as the optimum element A). FIG. 5 is a cross-section view showing the state in which the cuff 12 is wound around the upper arm 14. As shown in FIG. 5, the pressure-sensing elements 32 provided on the press surfaces 30 of the pressure-pulse-wave sensors 28 have respective different distances from the brachial artery 98 of the upper arm 14. Therefore, it is desirable that one of the pressure-sensing elements 32 that is located right above, or in the vicinity of, the brachial artery 98 be selected as the optimum element A that can detect, with the highest sensitivity, the pressure pulse wave. FIG. 6 shows a relationship between the pressure-sensing elements 32 and respective amplitudes of the pressure-pulse-wave signals SM detected by the elements 32. In the figure, the sequential numbers of the pressure-sensing elements 32 start with one of opposite ends of the array of elements 32 provided on the press surfaces 30. Respective amplitudes of pressure-pulse-wave signals SM detected by nearer pressure-sensing elements 32 to the brachial artery 98 are greater than those detected by remoter elements 32 from the artery 98. Therefore, the optimum-element selecting means 96 selects, as the optimum element A, one of the pressure-sensing elements 32 that provides a pressure-pulse-wave signal SM having a greater amplitude in the relationship shown in FIG. 6, most preferably, the element 32 that provides the signal SM having the greatest amplitude.

A heart-sound extracting means 100 subjects the pressure-pulse-wave signal SM supplied from the optimum element A, to a digital filter, and thereby extracts, from the signal SM, a heart-sound component having frequencies in a prescribed frequency band corresponding to a frequency band generally possessed by heart sounds. The thus extracted heart sounds are displayed on the display device 80. The prescribed frequency band may range from 30 to 600 Hz. A main component of the pressure-pulse-wave signal SM is the pressure pulse wave BAP produced from the brachial artery 98. However, heart sounds which are produced when the valves of the heart are opened and closed, propagate through the blood vessels. Therefore, the pressure-pulse-wave signal SM contains the heart-sound component. Thus, the heart sounds can be detected at the upper arm 14 by extracting, from the pressure-pulse-wave signal SM, a signal having frequencies in the frequency band generally had by heart sounds.

Figure 7:
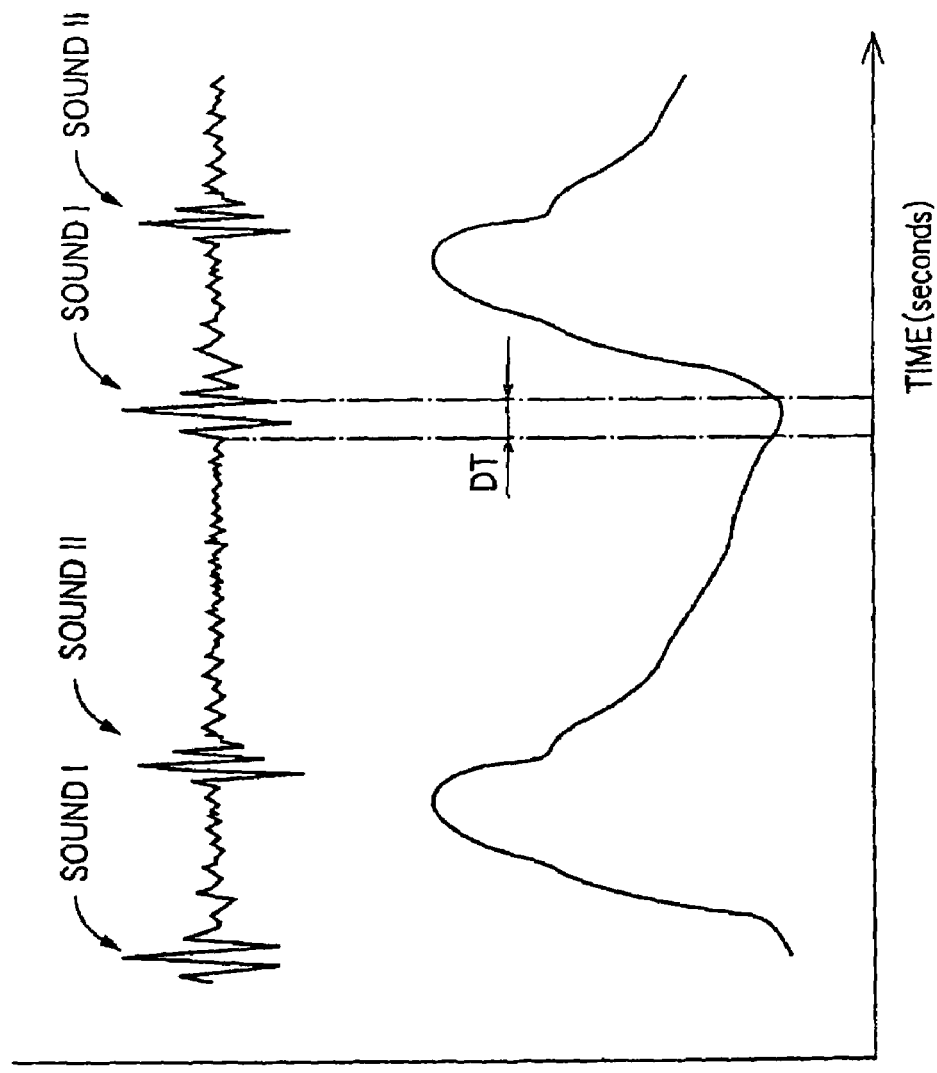
FIG. 7 is a graph showing heart sounds extracted by a heart-sound extracting means, and a pressure pulse wave BAP from which noise has been extracted by a noise removing means.

A noise removing means 102 subjects the pressure-pulse-wave signal SM supplied from the optimum element A, to a digital filter, and thereby removes noise from the signal SM, so as to extract the pressure pulse wave BAP produced when the brachial artery 98 pulsates. The signal SM from which noise has been removed is displayed on the display device 80. Since the pressure pulse wave BAP is a heartbeat-synchronous wave, the noise removing means 102 removes, from the signal SM, a component having frequencies not lower than 50 Hz. FIG. 7 shows heart sounds extracted by the heart-sound extracting means 100, and a pressure pulse wave BAP freed of noise by the noise removing means 102.

A pulse-wave-propagation-velocity-relating-information obtaining means 104 includes a time-difference determining means 106, and a pulse-wave-propagation-velocity determining means 108. The time-difference determining means 106 determines a timing when a prescribed periodic point of the heart sounds extracted by the heart-sound extracting means 100 is detected, and a timing when a prescribed periodic point of the pressure pulse wave BAP is detected, and determines a time difference DT (sec) between the two timings (i.e., a pulse-wave propagation time). The prescribed periodic point of the heart sounds may be a starting point (i.e., a rising point) of a first heart sound I, a peak point of a first heart sound I, a starting point of a second heart sound II, or a peak point of the second heart sound II. The prescribed periodic point of the pressure pulse wave BAP may be a rising point or a peak point of a heartbeat-synchronous pulse of the wave BAP. FIG. 7 shows a time difference DT between a rising point of a first heart sound I and a rising point of a corresponding heartbeat-synchronous pulse of a pressure pulse wave BAP.

The pulse-wave-propagation-velocity determining means 108 determines, based on the pulse-wave propagation time DT determined by the time-difference determining means 106, a pulse-wave propagation velocity PWV (m/sec), according to the following expression (1), pre-stored in the ROM 76:

$$PWV = L/DT \tag{1}$$

The thus determined pulse-wave propagation velocity PWV is displayed on the display device 80. In the above expression (1), L is a length of an artery from an initial end of the aorta to a portion thereof located right below the optimum element A, and is obtained in advance by experiments.

Figure 8:
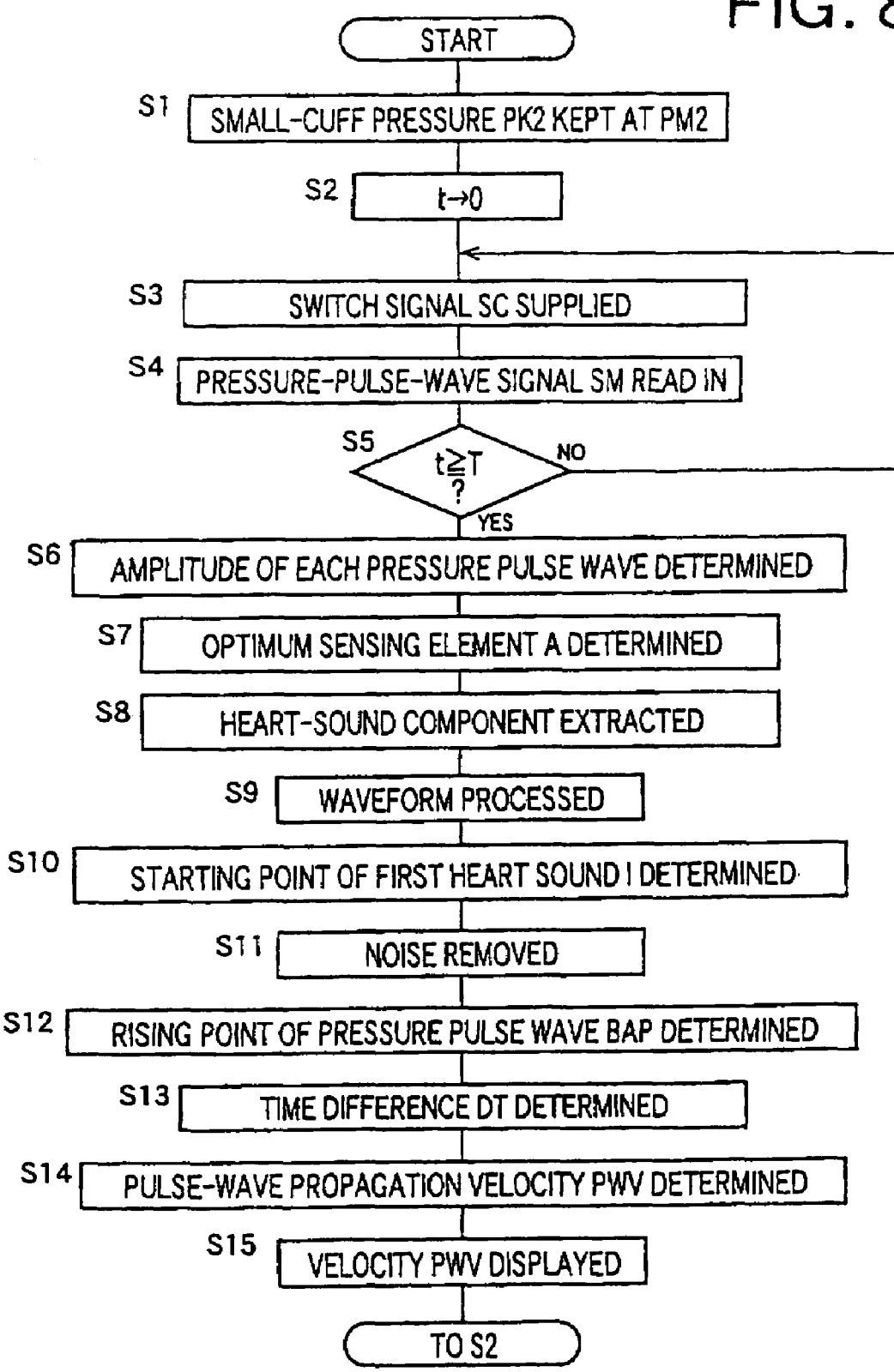
FIG. 8 is a flow chart representing a control program according to which the control device of FIG. 4 operates for determining a pulse-wave propagation velocity PWV.

FIG. 8 is a flow chart representing a control program according to which the control device 46 is operated, as shown in FIG. 4, to determine a pulse-wave propagation velocity PWV. The determination of pulse-wave propagation velocity PWV is carried out in a state in which the upper arm 14 is not pressed by the large cuff 18.

In FIG. 8, first, at Step S1 (hereinafter, "Step" is omitted) corresponding to the small-cuff-pressure control means 94, the control device 46 starts the air pump 56 and operates the pressure control valve 54, so that the pressing pressure $P_{K2}$ of the small cuff 20 is kept at a considerably low pressure of, e.g., 40 mmHg.

Next, at S2, a content of a timer t is replaced with "0", so that the timer t is reset to zero and, at S3, the control device 46 outputs the switch signal SC to switch the multiplexer 60 and the EPROM 64 at a period sufficiently shorter than an average pulse period. Then, at S4, the control device 46 reads in the pressure-pulse-wave signal SM supplied from the multiplexer 60.

Next, at S5, the control device 46 judges whether a time indicated by a number counted by the timer t has reached a prescribed reading-in period T. The reading-in period T may be equal to an average pulse period, i.e., a length of one average heartbeat-synchronous pulse. Each time one switch signal SC is supplied to the multiplexer 60 at S3, one of the respective pressure-pulse-wave signals SM detected by the sixty pressure-sensing elements 32 is supplied from the multiplexer 60 to the control device 46. While S3, S4 and S5 are repeated sixty times, all the signals SM detected by the sixty elements 32 are supplied from the multiplexer 60 to the control device 46.

Next, the control goes to S6 and S7 corresponding to the optimum-element selecting means 96. First, at S6, the control device 46 determines respective amplitudes of the respective pressure-pulse-wave signals SM which have been read in while S3, S4 and S5 are repeated. At S7, the control device 46 determines the greatest one of the respective amplitudes determined at S6, and determines, as the optimum element A, one of the pressure sensing elements 32 that provides the greatest amplitude.

Next, the control goes to S8 corresponding to the heart-sound extracting means 100. More specifically described, at S8, the control device 46 subjects the pressure-pulse-wave signal SM detected by the optimum element A selected at S7, to a digital filter, so as to extract a component having frequencies of from 30 to 600 Hz. Thus, the heart-sound component is extracted from the pressure-pulse-wave signal SM.

At S9, the control device 46 processes a waveform of the heart-sound component extracted at S8, so as to determine a prescribed periodic point on the waveform as one of two reference points to determine a pulse-wave propagation time DT. More specifically described, the waveform of the heart-sound component is subjected to a smoothing or differentiating process which is known as a useful technique to process a physical signal, and the thus processed waveform is further subjected to a squaring process. Thus, the amplitude of the waveform of heart sounds, measured from a baseline representing a signal level when no heart sounds are detected, is squared.

Next, at S10, the control device 46 determines, based on the waveform whose amplitude has been squared at S9, a starting point of a first heart sound I as the first reference point to determine the pulse-wave propagation time DT. Then, at S11 corresponding to the noise removing means 102, the control device 46 subjects the pressure-pulse-wave signal SM detected by the optimum element A, to a digital filter to remove a component having frequencies not lower than 50 Hz. Thus, a pressure pulse wave BAP free of noise is extracted from the pressure-pulse-wave sensor SM.

Subsequently, at S12, the control device 46 determines, based on the pressure pulse wave BAP extracted at S11, a rising point of the wave BAP that corresponds to the starting point of the first heart sound I. The rising point of the wave BAP is the second reference point to determine the pulse-wave propagation time DT. Next, at S13 corresponding to the time-difference determining means 104, the control device 46 determines a time difference DT between the time when the starting point of the first heart sound I determined at S10 was detected, and the time when the rising point of the pressure pulse wave BAP determined at S12 was detected.

Then, at S14 corresponding to the pulse-wave-propagation-velocity determining means 106, the control device 46 determines a pulse-wave propagation velocity PWV by replacing the parameter DT of the expression (1) with the time difference DT determined at S13. Next, at S15, the thus determined pulse-wave propagation velocity PWV is displayed on the display device 80. After S15, the control goes back to S2. Thus, heart sounds are continuously detected and pulse-wave propagation velocities PWV are continuously determined.

In the illustrated embodiment, the heart-sound extracting means 100 (S8) extracts the heart-sound component representing the heart sounds, from the pressure-pulse-wave signal SM provided by the pressure-pulse-wave sensor 28 worn on the upper arm 14. Thus, the heart sounds can be detected at a position distant from the chest.

In the illustrated embodiment, the optimum-element selecting means 96 (S7) selects, from the plurality of pressure-sensing semiconductor elements 32, the optimum element A that can detect, with the highest sensitivity, the pressure pulse wave BAP, and the heart-sound component is extracted from the pressure-pulse-wave signal SM provided by the optimum element A. Thus, heart sounds having a clear waveform can be detected.

In the illustrated embodiment, the pressure-pulse-wave 28 detects two sorts of heartbeat-synchronous signals, i.e., the heart sounds and the pressure pulse wave BAP, and the pulse-wave-propagation-velocity determining means 106 (S14) determines the pulse-wave propagation velocity PWV based on the heart sounds and the pressure pulse wave BAP. Thus, the single pressure-pulse-wave sensor 28 suffices for determining the pulse-wave propagation velocity PWV, and accordingly it can be easily worn on the patient.

In the illustrated embodiment, when the cuff 12 is wound around the upper arm 14 to measure a blood pressure of a living subject, simultaneously the pressure-pulse-wave sensor 28 to detect the heart sounds is worn on the subject. Since the cuff 12 is adapted to be closely wound around a body portion of a living subject, that the cuff 12 is wound around the upper arm 14 means that the pressure-pulse-wave sensor 28 is appropriately worn on the upper arm 14.

While the present invention has been described in its preferred embodiment by reference to the drawings, it is to be understood that the invention may otherwise be embodied.

For example, in the illustrated physical-information obtaining apparatus 10, the pressure-pulse-wave sensor 28 is adapted to be worn on the upper arm 14. However, the sensor 28 may be adapted to be worn on a neck or a wrist.

In the illustrated physical-information obtaining apparatus 10, the heart-sound extracting means 100 comprises the digital filter, i.e., software. However, the extracting means 100 may comprise an analog filter which is provided by resistors, capacitors, etc.

The illustrated physical-information obtaining apparatus 10 employs the four pressure-pulse-wave sensors 28 each of which includes the fifteen pressure-sensing semiconductor elements 32, i.e., the sixty pressure-sensing elements 32, in total, to detect the respective pressure-pulse-wave signals SM. However, the number of the pressure-sensing elements 32 is not limited to sixty, but may be one only.

Each of the pressure-pulse-wave sensors 28 includes the pressure-sensing semiconductor elements 32 to detect the respective pressure pulse waves. However, it is possible to employ a different type of pressure sensor, e.g., a diaphragm-type pressure sensor that utilizes the change of resistance of a strain gauge, formed in a diaphragm, when the gauge is displaced by a pressure exerted thereto. In addition, the cuff-pulse-wave signal SW extracted by the high-pass filter 42 and the low-pass filter 48 from the first pressure signal $SP_1$ provided by the pressure sensor 34, also represents a pressure pulse wave BAP produced from the brachial artery 98. Therefore, the pressure sensor 34, the high-pass filter 42, and the low-pass filter 48 may be used as a pressure-pulse-wave sensor.

It is to be understood that the present invention may be embodied with other changes, improvements and modifications that may occur to a person skilled in the art without departing from the spirit and scope of the invention defined in the appended claims.

What is claimed is:

1. An apparatus for obtaining information relating to a velocity at which a pulse wave propagates through an artery of a body portion of a living subject, the apparatus comprising:

a heart-sound detecting apparatus comprising a pressure-pulse-wave sensor which is adapted to be worn on the body portion of the subject that is distant from a chest of the subject, detects a pressure pulse wave produced by the artery of the body portion, and generates a pressure-pulse-wave signal representing the detected pressure pulse wave, and a heart-sound extracting means for extracting, from the pressure-pulse-wave signal generated by the pressure-pulse-wave sensor, a heart-sound component representing a heart sound of the subject; and an information obtaining means for obtaining said information based on a first timing at which the pressurepulse-wave sensor of the heart-sound detecting apparatus detects a prescribed periodic portion of the heart sound, and a second timing at which the pressure-pulse-wave sensor detects a prescribed periodic portion of the pressure pulse wave;

wherein the information obtaining means comprises means for obtaining, as said information, a time difference between the first and second timings.

2. An apparatus according to claim 1, wherein the information obtaining means comprises means for obtaining, as said information, said velocity by dividing, by said time difference, a distance between a heart of the subject and the body portion thereof distant from the chest thereof.

* * * * *